(12) United States Patent
Luo et al.

(10) Patent No.: US 7,852,981 B2
(45) Date of Patent: Dec. 14, 2010

(54) DETECTOR DEVICE AND CT INSPECTION SYSTEM HAVING THE SAME

(75) Inventors: Xilei Luo, Beijing (CN); Zhiqiang Chen, Beijing (CN); Yuanjing Li, Beijing (CN); Yulan Li, Beijing (CN); Yinong Liu, Beijing (CN); Li Zhang, Beijing (CN); Ziran Zhao, Beijing (CN); Wanlong Wu, Beijing (CN); Shuqing Zhao, Beijing (CN); Bin Sang, Beijing (CN); Hailin Wang, Beijing (CN); Shuo Cao, Beijing (CN); Dong Lin, Beijing (CN); Zhimin Zheng, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 86 days.

(21) Appl. No.: 12/318,190

(22) Filed: Dec. 23, 2008

(65) Prior Publication Data
US 2009/0168948 A1 Jul. 2, 2009

(30) Foreign Application Priority Data
Dec. 29, 2007 (CN) .......................... 2007 1 0308551

(51) Int. Cl.
*A61B 6/03* (2006.01)
*H05G 1/64* (2006.01)
(52) U.S. Cl. .................. 378/19; 378/189; 250/370.09
(58) Field of Classification Search .................. 378/19, 378/98.8, 189; 250/370.09
See application file for complete search history.

(56) References Cited

U.S. PATENT DOCUMENTS

| 4,417,353 | A | * | 11/1983 | Groh et al. ..................... 378/4 |
| 4,560,877 | A | * | 12/1985 | Hoffman ..................... 250/366 |
| 4,626,688 | A | * | 12/1986 | Barnes ................... 250/361 R |
| 5,444,752 | A | * | 8/1995 | Dobbs et al. .................. 378/19 |
| 5,487,098 | A | * | 1/1996 | Dobbs et al. .................. 378/19 |
| 5,768,331 | A | * | 6/1998 | Gordon et al. ................ 378/19 |
| 5,799,057 | A | * | 8/1998 | Hoffman et al. ............ 378/147 |
| 5,848,116 | A | * | 12/1998 | Sugihara ...................... 378/19 |
| 5,991,357 | A | * | 11/1999 | Marcovici et al. ............. 378/19 |
| 6,411,672 | B1 | * | 6/2002 | Sasaki et al. .................. 378/19 |
| 6,587,538 | B2 | * | 7/2003 | Igarashi et al. ................ 378/19 |
| 7,135,687 | B2 | * | 11/2006 | Lacey et al. ............ 250/370.15 |
| 7,177,387 | B2 | * | 2/2007 | Yasunaga et al. .............. 378/19 |
| 7,372,938 | B2 | * | 5/2008 | Pohan et al. .................. 378/19 |
| 7,489,516 | B2 | * | 2/2009 | Lacey ......................... 361/759 |

\* cited by examiner

*Primary Examiner*—Allen C. Ho
(74) *Attorney, Agent, or Firm*—Jacobson Holman PLLC

(57) ABSTRACT

Disclosed is a detector device, comprising: an adjustable positioning base and a detector module. The adjustable positioning base includes: a horizontal plate being able to fixedly connect onto an annular rotation table or disk; and a vertical plate extending from the horizontal plate and generally perpendicular to the horizontal plate. A horizontal through long groove is provided at one side of the vertical plate, and the detector module is able to fixedly installed in said horizontal through long groove of the adjustable positioning base. By employing the technical solution defined in the present invention, the detector device has a compact structure, and precision adjustment and positioning for the detector device can be achieved. In addition, the present invention also provides a CT inspection system having the above detector device.

29 Claims, 7 Drawing Sheets

DETECTOR DEVICE AND CT INSPECTION SYSTEM HAVING THE SAME

FIELD OF INVENTION

The present invention belongs to the technical field of radiation detecting, which relates to a CT security inspection system, particularly, to a detector device used for a CT security inspection system, more particularly, to a detector device use for a CT security inspection system having a collimator and being adjustable and precisely positioned.

BACKGROUND OF INVENTION

In the detector device in the prior art for CT security inspection system, a detector array in the detector module is arranged on the positioning support, an adjustable collimator is generally installed in front of the detector module, thereby, the entire detector device is structured. The structured detector device described above has the following shortages and problems: first, the volume of the detector device employing the above structure is too big, therefore, the space occupied by the entire CT security inspection system is increased; second, since it is required to adjust related position relationship among the radiation source, the collimator, the detector module and the positioning support, the adjusting operation, especially the adjustment for the collimator, is complicated, so that the installation and the regulating for the position of the detector device are inaccurate. Furthermore, since the sealing of the detector device is not very good, the detector crystal has a poor working stability.

SUMMARY OF INVENTION

Accordingly, an object of the present invention is intended to overcome at least one aspect of the shortages and problems existing in the prior art.

Accordingly, one of other objects of the present invention is to provide a detector device having a compact structure.

In addition, another object of the present invention is to provide a detector device having a collimator and being able to be precisely adjusted and positioned, wherein a detector installed thereon can be precisely adjusted so as to be adopted in the CT inspection system.

Still another object of the present invention is to provide a CT inspection system to rapidly and easily adjust and position the detector device.

Still a further object of the present invention is to provide a detector device protected from the interference caused by electromagnetic waves, temperature and humidity so that the working stability of the detector device is ensured.

According to an aspect of the present invention, it provides a detector device comprising: an adjustable positioning base, which includes: a first plate being able to be fixedly connected onto an annular rotation table or disk perpendicular to the rotation axis of the table or disk; and a second plate extending from the first plate and generally being perpendicular to the first plate, wherein a horizontal through long groove is provided at one side of the second plate; and a detector module, which is able to be fixedly installed in the horizontal through long groove of the adjustable positioning base.

In one embodiment, a zigzag structure is provided at the top of one side of the second plate, the zigzag structure is formed by alternating convex and concave portions, the concave portion is used for receiving transmission wires of the detector module.

Preferably, a notch is further provided at the bottom of the horizontal through long groove, and radiation protection material is embedded in the notch.

In one embodiment, the first plate is provided with at least one convex stage, a guide slot is formed as an opening in the at least one convex stage, and a limiting guide wheel is provided in the guide slot and is able to slide along the guide slot.

Furthermore, the at least one convex stage is further provided with a micrometer head fixed onto the annular rotation disk through a support for adjusting the position of the detector device and locking the detector device.

Alternatively, the at least one convex stage includes two convex stages, the micrometer head is respectively provided on the two convex stages, and the micrometer head is fixed onto the annular rotation table or disk through the support, for adjusting the position of the detector device and locking the detector device.

In one embodiment, a projection of the adjustable positioning base on a plane perpendicular to the rotation axis, has a shape selected from one of an arc, angled line segments, a straight line and multiple sections of arcs.

In another embodiment, the shape of the cross section of the adjustable positioning base on a plane parallel to the rotation axis is substantially an inverted T-shape.

In a further embodiment, the detector device further comprises a data collection circuit provided at another side on the second plate, where is opposite to the side on which the detector module is provided, for collecting the data produced by the detector module.

Preferably, radiation protection material for preventing radiation from penetrating therethrough is provided at the side of the second plate on which the detector module is provided.

In one embodiment, the detector module comprises a two-level energy detector array constituted by a high energy detector array and a low energy detector array.

In another embodiment, the detector module further comprises a collimator integrated in front of the detector module, the collimator including: a base having comb structures opposing each other in an up-and-down manner; and radiation protection partition boards provided between the comb structures opposing each other up-and-down for preventing radiation from penetrating therebetween.

Preferably, the detector module further comprises a shielding cover for covering the adjustable positioning base and detector module, and a window is formed as an opening at a place where the shielding faces opposite to the detector module, and a foil is connected to the window to cover the window. The shielding cover is used to shield any electromagnet field and any variation of the outside environment that may cause interference to the detector module.

Preferably, the limitation guide wheel is constituted by a high-precision bearing and a pin roll fitted with the high-precision bearing.

According to another aspect of the present invention, a CT inspection system is provided, comprising: a rotation disk rotating about a rotation axis $A_R$ parallel to a direction along which an object to be inspected enters into an inspection passage; a radiation source provided at one side of the rotation disk, for generating radiation rays; a detector device provided at another side of the rotation disk generally opposing the radiation source, the detector device comprises: an adjustable positioning base being able to be fixedly connected onto the rotation disk; and a detector module fixedly installed onto the adjustable positioning base, wherein the adjustable position base includes: a first plate being able to be fixedly connected onto the annular rotation disk perpendicular to the rotation axis of the annular rotation disk; and a second plate extending from the first plate and being substantially perpendicular to the first plate, wherein the detector module is able to be fixedly installed on the second plate of the adjustable positioning base.

In one embodiment, the CT inspection system further comprises: a data collection system for receiving and processing the data signal produced by the detector module.

Preferably, the CT inspection system further comprises: a radiation source control unit for supplying electrical power to the radiation source to control the operation of the radiation source.

In another embodiment, the radiation source is one of an X-ray source, an isotope radiation source and a gamma-ray source.

At least one aspect of above technical solutions of the present invention has the following advantages:

Since the detector module is installed onto the adjustable positioning support, more particularly, into the positioning groove of the inverted T-shaped adjustable positioning base, a detector device with a compact structure can be obtained. Furthermore, with the above technical solutions, the precise positioning during the installation of the detector device can be achieved without any other separate or additional adjusting collimator. In addition, since the shielding cover seals the detector module, it will not experience interference from electromagnetic waves, or variation of the temperature and humidity, so that the working stability of the detector device is ensured.

DETAILED DESCRIPTION OF PREFERRED EMBODIMENTS

Figure 1:
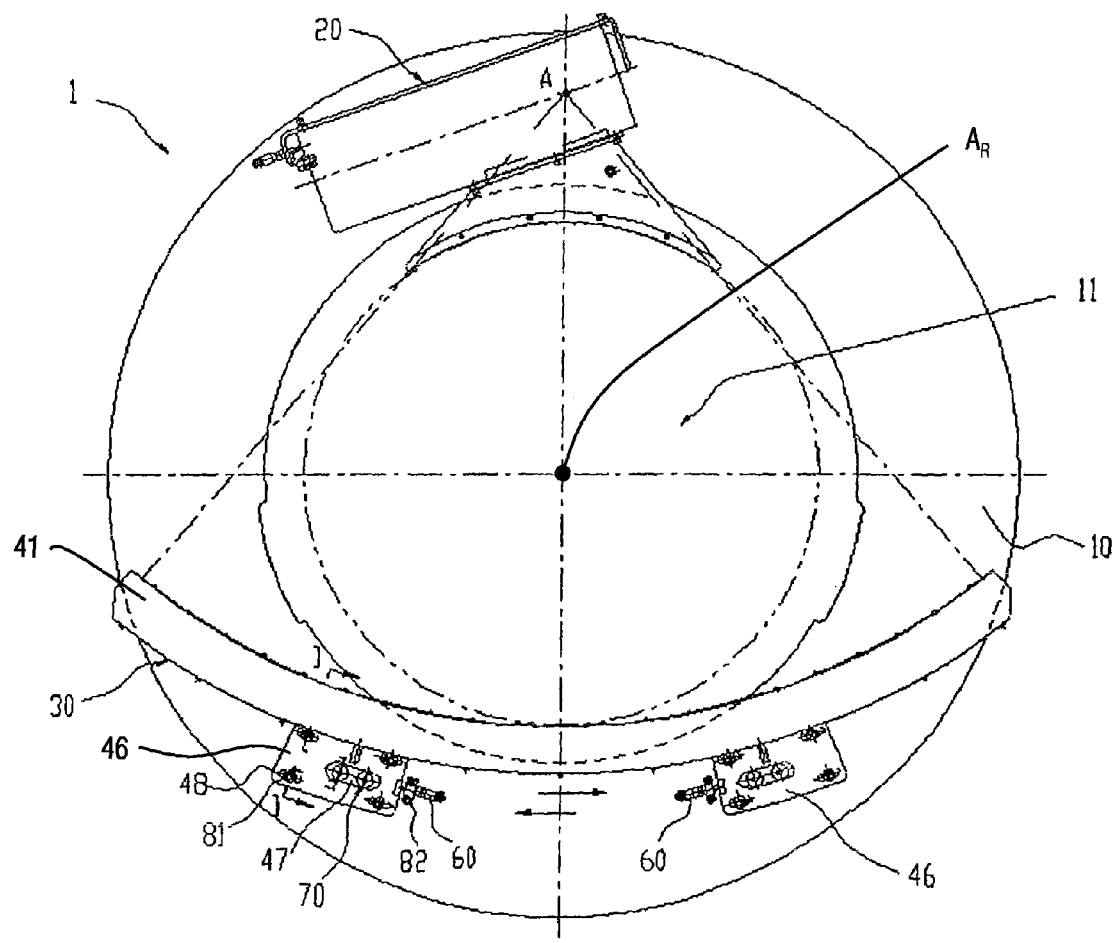
FIG. 1 is a top view of a CT inspection system having a detector device according to an embodiment of the present invention.

Preferred embodiments of the present invention will be described hereinafter in detail with reference to the attached drawings, wherein like reference numerals refer to like elements throughout the specification. The present invention may, however, be embodied in many different forms and should not be construed as being limited to the embodiments set forth herein; rather, these embodiments are provided so that the present disclosure will be thorough and complete, and will fully convey the concept of the invention to those skilled in the art.

FIG. 1 shows a CT inspection system 1 including a detector device according to one embodiment of the present invention. As shown in FIG. 1, the CT inspection system includes an annular rotation table or a disk 10 provided inside a door-shaped frame (not shown), for rotating about a rotation axis $A_R$ (referring to the central axis perpendicularly passing through the paper in FIG. 1) under the driving action of a driving device (not shown). Preferably, the rotation axis $A_R$ is parallel to a direction along which the object to be inspected, for example, luggage, enters into an inspection passage 11 of the inspection system 1.

CT inspection system 1 further comprises a radiation source 20 and a detector device 30, which are provided on positions on the rotation table or disk 10 opposing each other. In an embodiment, the radiation source 20 is one of an X-ray source, an isotope radiation source and a gamma-ray source. According to the embodiment of the present invention, referring to FIG. 2, the detector device 30 comprises an adjustable positioning base 40 and a detector module 50 fixedly connected onto the adjustable positioning base 40.

In addition, the CT inspection system 1 further comprises a data collection system (not shown in the Figures) for receiving and processing the data signal produced by the detector module; and a radiation source control unit (not shown in the Figures) for supplying electric power to the radiation source to control the operation of the radiation source in different conditions. In a further preferred embodiment, the CT inspection system 1 is preferably configured with a computer system for processing the output of the data collection system and producing a signal necessary for operating and controlling of the CT inspection system 1.

In an embodiment, after a tapered radiation beam generated by the radiation source 20 is passed through the object to be inspected, for example luggage, which is transferred forwardly along the inspection passage 11, it is received by the detector module 50 on the detector device 30, and then, a signal representing the density of the object to be inspected is produced from the detector module 50. At the same time, the annular rotation table or disk 10 is rotated about the rotation axis $A_R$ thereof, so that the radiation source 20 and the detector device 30 are also rotated about the rotation axis $A_R$ and the inspection passage 11. As a result, each of the plurality of projections is generated at each of the plurality of the angles of projections. Next, the signal produced by the detector module 50 is received and processed by the data collection system (not shown) so as to determine the suspicious contents or the like in the object to be inspected based on the processed result.

Figure 2:
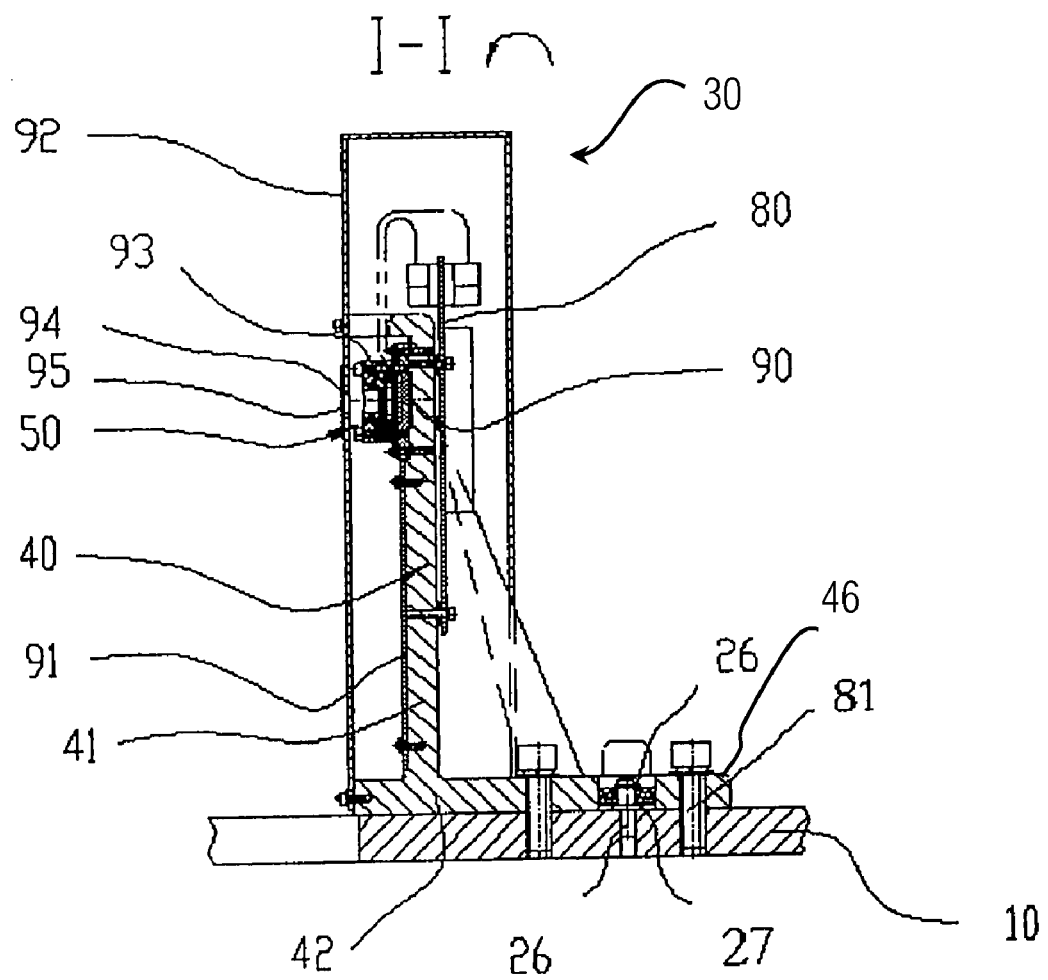
FIG. 2 is a section view taken along I-I line of the detector device of FIG. 1.
Figure 3:
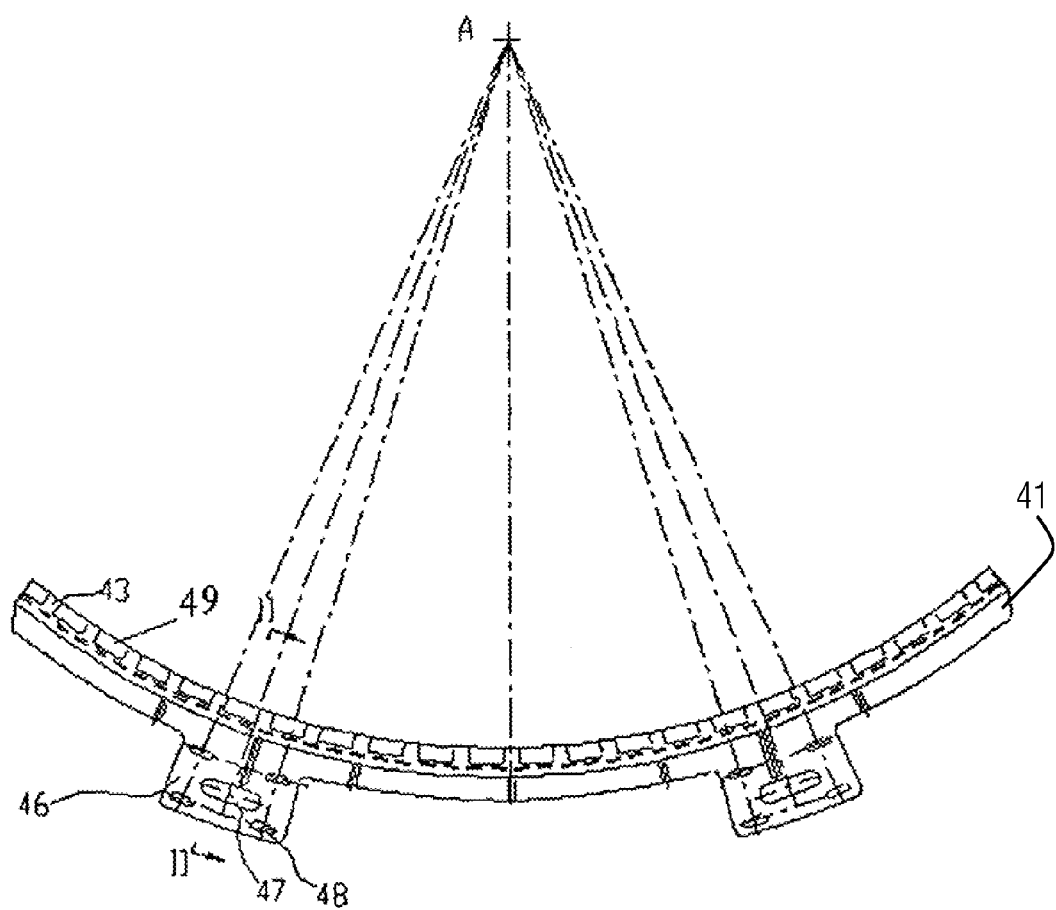
FIG. 3 is a top view of an inverted T-shaped adjustable positioning base of the detector device according an embodiment of the present invention.

Referring to FIG. 2, the detector device 30 comprises an adjustable positioning base 40 and a module 50 fixedly connected onto the adjustable positioning base 40. As shown in FIGS. 1 and 3, the detector device 30 is provided on the annular rotation table or disk 10 along a section of arc generally centered at a target A of the radiation source 20, and opposite to or opposing the target A of the radiation source 20 with respect to the inspection passage 11. It should be noted that, although in the above embodiment, the adjustable positioning base 40 and the detector module 50 are provided along the section of arc generally centered at the target A of the radiation source 20, the present invention is not limited thereto, and any other alternative form can be applied. For example, the detector device 30 can be configured to be angled line segments connected with predetermined angles at both sides of the inspection passage 11. In one embodiment, the detector device can also be configured to be two or more sections of arc generally centered at the target A of the radiation source 20 parallel to each other about the inspection passage 11. In another embodiment, the detector device 30 can be further configured to be one section of a straight line opposing the target A of the radiation source 20.

Figure 4:
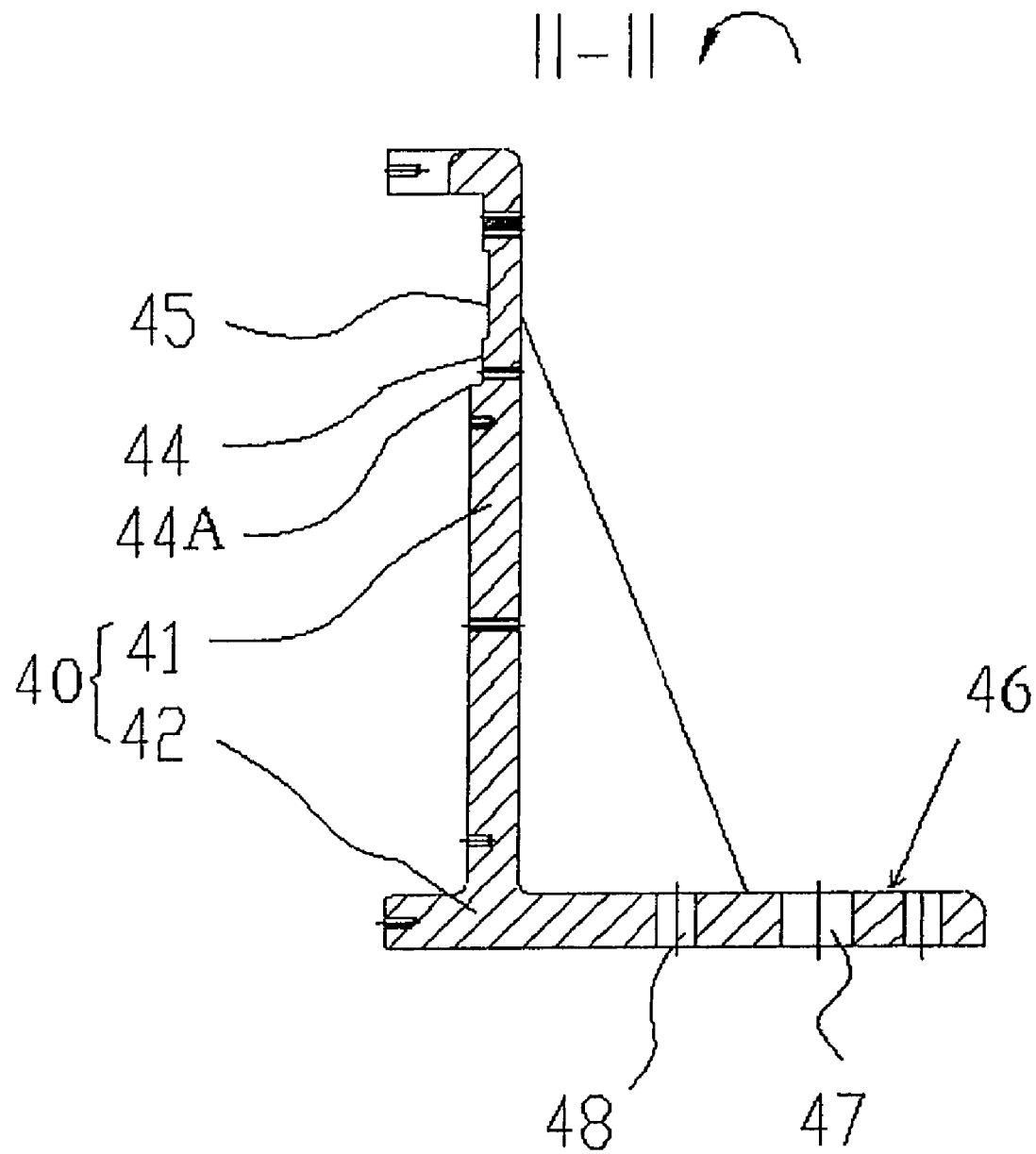
FIG. 4 is a section view taken along II-II of FIG. 3.

FIG. 2 is a sectional view illustrating the detector device 30 taken along a straight line I-I connecting the target A of the radiation source 20 to the detector device 30. FIG. 3 is a top view illustrating the adjustable positioning base 40 of the detector device 30. FIG. 4 is a sectional view taken along the straight line II-II connecting the target A of the radiation source 20 to the detector device 30. For clearer illustration, in FIG. 4, the detector module 50 fixedly connected onto the adjustable positioning base 40 is removed.

As shown in FIG. 4, the adjustable positioning base 40 is constituted by an arched second plate 41 and an arched first plate 42 being able to fix on the annular rotation table or disk 10. As shown in FIG. 3, the projection of the arched second plate 41 and the arched first plate 42 on a plane perpendicular to the rotation axis $A_R$ is a section of arc generally centered at the target A of the radiation source 20. It will be appreciated from the Figures that if the annular rotation table or disk 10 is oriented vertically, then the rotation axis $A_R$ and the second plate 41 will be oriented horizontally, and that the first plate 42 will be oriented vertically. As shown in FIG. 4, in the cross section taken along the straight line II-II connected the target A of the source radiation 20 to the detector device 30, the adjustable positioning base 40 has an inverted T-shape. One side of the arched second plate 41 is uniformly provided with a concave-convex portion with an alternating concave and convex profile, as shown in FIG. 3, the concave-convex portion is constituted by a concave portion 49 and a convex portion 43. The concave portion 49 is used for arranging transmission wires of the detector module 50 so as to easily facilitate management of the wiring of the transmission wires. Also, by employing the above configuration, space in the detector device is saved, thereby the structure of the detector device is more compact.

As shown in FIG. 4, a through long groove 44 perpendicular to the rotation axis $A_R$ is provided at the position which is at the same side as the zigzag concave-convex step on the arched second plate 41, i.e., the side opposite to the radiation source 20, so that step portions 44A are formed at both ends of the through long groove 44. When the detector module 50 is installed in the through long groove 44 of the arched second plate 41 of the adjustable positioning base 40, step portions 44A are used for positioning reference of the detector module 50 so as to rapidly and easily position the detector module 50.

In an embodiment, a shallow notch 45 opens at the bottom surface of the through long groove 44. Before the detector module 50 is installed to the through long groove 44 of the arched second plate 41 of the adjustable positioning base 40, a radiation protection material 90 is embedded in the shallow notch 45. Further, as shown in FIG. 2, radiation protection material 91 also covers the remaining portion of the front surface (the surface facing the radiation source 20) of the arched second plate 41 on which the detector module 50 is installed. The radiation protection material 91 is the same as the radiation protection material 90 embedded in the shallow notch 45, or they can be different from each other. In an embodiment, the radiation protection material 90 and 91 may be one selected from the metals Pb or W. Through providing radiation protection material on the surface, facing the radiation source 20, of the arched second plate 41, a data collection circuit 80 at the rear surface of the arched second plate 41 is effectively protected from the damage caused by radiation passing through.

Referring to FIGS. 1-3, two convex stages 46 symmetrically protrude from the arched first plate 42 of the adjustable positioning base 40. An arched guide slot 47 and an arched bolt hole 48 are formed as separate openings on convex stages 46. Limiting guide wheel 70 is fixed in the arched guide slot 47 and able to slide along the arched guide slot 47, thereby, the movement track of the detector device 30 is defined. Although two convex stages 46 are symmetrically provided on the arched first plate 42 in above embodiment of the present invention, the present invention is not limited thereto, the number of convex stages can be one or more. In one preferred embodiment, the limiting guide wheel 70 is formed by a pin roll 26 with steps and a high-precision bearing 27, thus it is ensured that the limiting guide wheel 70 precisely moves along the arched guide slot 47, and the distance offset of the detector device 30 in respect to the target A of the radiation source in the direction of the circumference of the arched section is reduced.

Referring to FIG. 1, a micrometer head 60 is provided at one side of the convex stage 46, for adjusting the position of the detector device 30 and locking the detector device 30. The micrometer head 60 is fixed on the annular rotation table or disk 10 through a support 82. In a preferred embodiment, in order to prevent displacement when the detector device 30 is being rotated along with the annular rotation table or the disk 10, the micrometer head 60 is respectively and symmetrically provided at both sides of the convex stage 46. Thereby, when the detector device 30 is rotated along with the annular rotation table or disk 10, the two micrometer heads 60 are able to produce a self-locking function, therefore, undesirable displacement is effectively avoided. Furthermore, a fastening screw 81 is provided on the convex stage 46, after the position of the detector device 30 is adjusted, the fasten screw 81 is screwed into the arched bolt hole 48, so that the detector device 30 is further fixed on the annular rotation table or disk 10.

Figure 5:
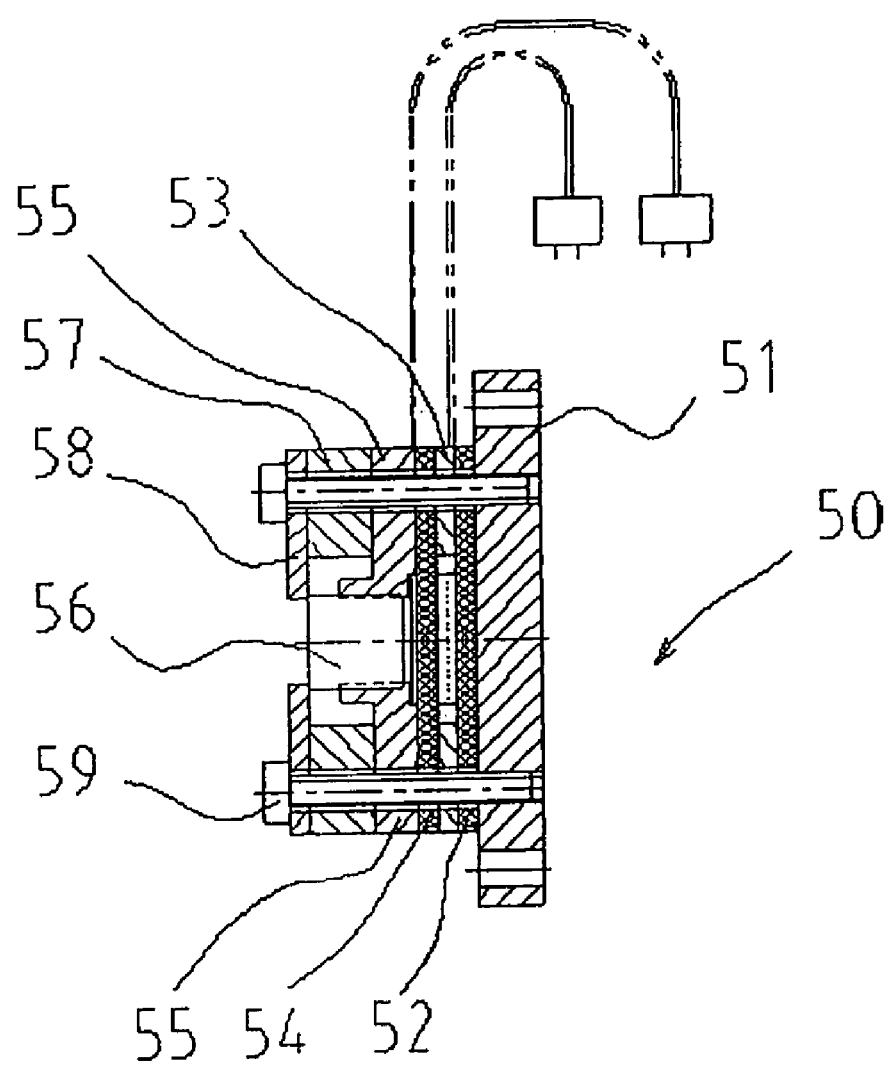
FIG. 5 is a front section view of the high, low energy detector module having a grid collimator according to an embodiment of the present invention.
Figure 6:
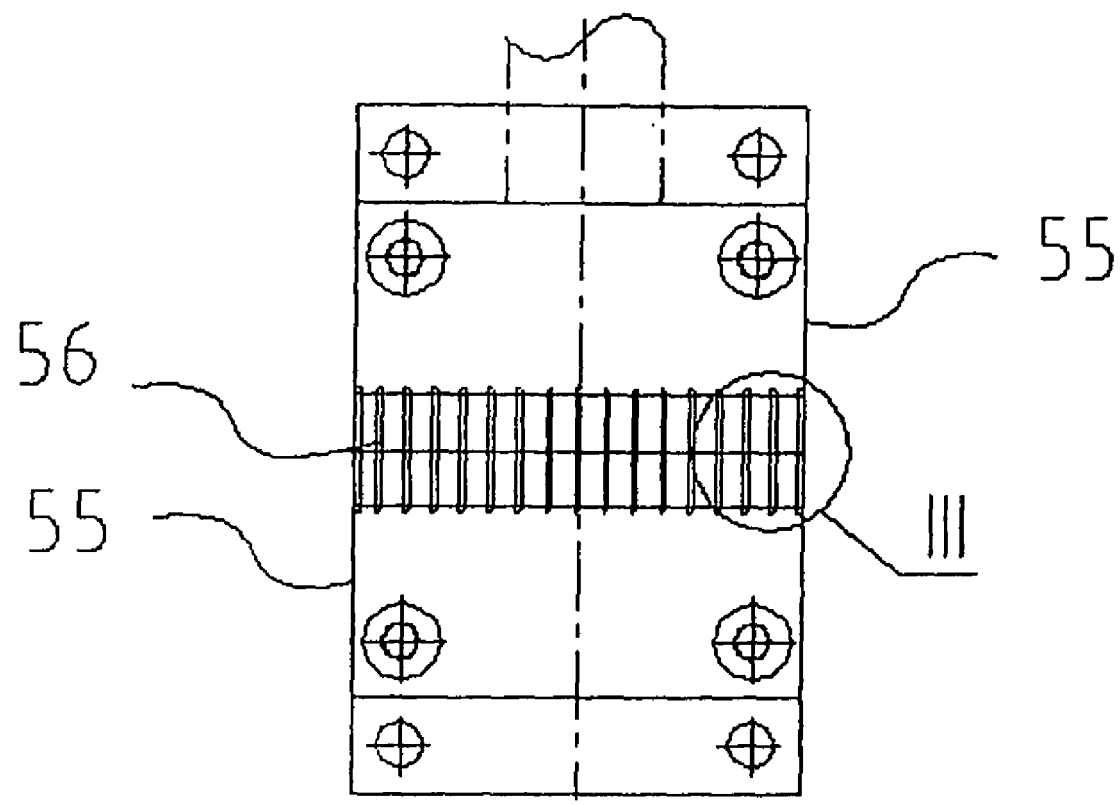
FIG. 6 is a left side view of FIG. 5.
Figure 7:
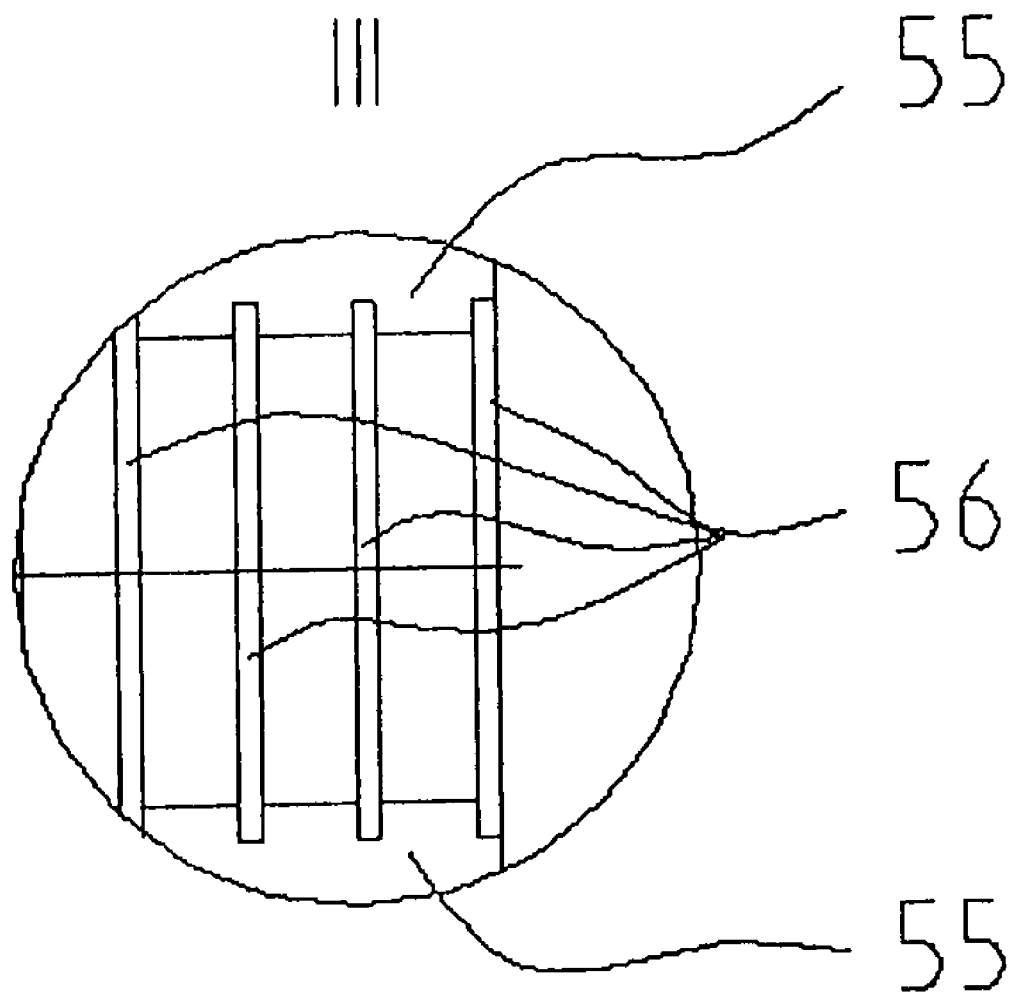
FIG. 7 is a partial enlarge view of FIG. 6.

Hereafter, referring to FIGS. 5-7, the structure of the detector module 50 according to an embodiment of the present invention is described. As shown in FIGS. 5 and 6, in an embodiment, the detector module 50 comprises a bottom plate 51, a high energy crystal circuit 52 as a high energy detector array provided at a front surface of the bottom plate 51, i.e., the surface facing the radiation source, a low energy crystal circuit 54 as a low energy detector array, and a partition board 53 provided between the high energy crystal circuit 52 and the low energy crystal circuit 54. Therefore, the structure of two-level-energy detector arrays is formed by employing the above high energy crystal circuit 52 and the low energy crystal circuit 54.

Although the detector module in the above embodiment employs a structure of two-level-energy detector arrays, the present invention is not limited thereto. For example, the detector module may employ a structure of a single-level-energy detector array or detector arrays of multi-levels of energy, of which the number of levels is more than two. When the single-level-energy detector array structure is employed, the partition board 53 is accordingly removed. When the structure of multi-levels energy detector arrays, of which the number of levels is more than two, is employed, a plurality of partition boards 53 may be provided between two of a plurality of detector arrays.

In addition, as shown in FIG. 5, a collimator is further integrally provided in front of the detector array structure, for collimating and calibrating the radiation emitted from the radiation source. As shown in FIGS. 6 and 7, the collimator comprises a base 55 with a structure having comb portions opposite to each other in a up-and-down manner, a plurality of partition boards 56 preventing the radiation from passing through, the plurality of partition boards 56 respectively provided in comb portions opposite to each other in up-and-down manner on the base 55, each detector crystal is provided between two adjacent comb portions. Thereby, a collimator having a grid structure is formed by employing the above configuration. Furthermore, as shown in FIG. 5, the collimator further comprises a radiation protection plate 58 provided to face to one side of the radiation source, and a spacer 57 is further provided between the radiation protection plate 58 and the base 55, for increasing the distance between the radiation protection plate 58 and the base 55.

In the above structure, since the collimator is directly integrated in the detector module 50, the structure of the detector module 50 is more compact, and a complicated adjusting and positioning process for the collimator in respect to the detector module is avoided. Structural components of above detector module 50 are assembled by screws 59, thereby the detector module 50 is structured.

It should be noted that, in the above embodiment, the detector module 50 employs the two-level energy detector having the high energy crystal circuit 52 and the low energy crystal circuit 54. However, the present invention is not limited thereto, a single-level energy detector or a multi-level energy detector may be employed.

Referring to FIGS. 2 and 4, the detector module 50 structured as above is mounted in the through long groove 44 of the arched second plate 41 of the adjustable positioning base 40, so that the detector device 30 is formed. As shown in FIG. 2, in an embodiment, a shielding cover 92 is provided at the outside of the adjustable positioning base 40, which is used for covering the adjustable positioning base 40 and the detector module 50 and for shielding electromagnetism as well as environmental changes. An elongated window 94 opens in a surface, which faces a detector crystal 93, of the shielding cover 92 to allow the radiation to enter into the detector module 50. Since the shielding cover 92 seals the detector module 50, the detector 50 is not interfered with by electromagnetic waves, or variations of temperature and humidity, so that the working stability of the detector device 30 is ensured. In order to control and adjust the radiation energy level introduced onto the detector module, metal foil is provided at the window 94, for example, aluminum foil 95 is connected to the window 94 to cover it.

Next, the positioning process of the detector device 30 according to the present invention is further described by referring to FIGS. 1-3.

As described above, the detector module 50 is mounted into the through long groove 44 of the arched second plate 41 of the adjustable positioning base 40, such that the detector device 30 is structured. Compared with the technical solution in the prior art, in which the detector array is arranged on the positioning support, the detector module 50 uses the step portion 44A of the horizontal through long groove 44 as a positioning reference thereof, so that the detector device 50 can be positioned rapidly and easily. At the same time, since positioning for the detector module 50 is achieved by employing the adjustable positioning base 40, adjusting and positioning for the detector array as in the prior art are avoided.

Next, the detector device 30 is mounting onto the annular rotation table or disk 10 of the CT inspection system 1. Here, all of fastening screws 81 are released, any one of micrometer heads 60 is initially rotated to make it retract back, and then another micrometer head is rotated to allow it to push the convex stage 46 to move forwardly. Here, under the guiding of the limiting guide wheel 70 inside the arched guide slot 47 of the convex stage 46, the detector device 30 is rotated about the target A of the radiation source 20 along a predetermined track defined by the arched guide slot 47, so that the precise positioning for the detector device 30 is achieved. After the adjusting and positioning for the detector device 30 is completed, fastening screws 81 are screwed into arched bolt holes 48, so that the detector device 30 is further fastened onto the annular rotation table or disk 10. Thereby, adjusting and positioning for the detector device 30 are completed.

Although a few embodiments of the present invention have been shown and described, it would be appreciated by those skilled in the art that changes may be made in these embodiments without departing from the principles and spirit of the invention, the scope of which is defined in the claims and their equivalents.

The invention claimed is:

1. A detector device for use on an annular rotation table or disk having a rotation axis, comprising:
   an adjustable positioning base, including:
      a first plate being able to be fixedly connected onto the annular rotation table or disk, perpendicular to the rotation axis of the annular rotation table or disk; and
      a second plate extending from said first plate and substantially perpendicular to the first plate, wherein a through long groove is provided at one side of the second plate, perpendicular to the rotation axis of the annular rotation table or disk; and
   a detector module, which is able to be fixedly installed in said through long groove of the adjustable positioning base.

2. The detector device as claimed in claim 1, wherein a zigzag structure is provided at the top of one side of the second plate, said zigzag structure is formed by alternating convex and concave portions, and said concave portions are used for receiving transmission wires of the detector module.

3. The detector device as claimed in claim 1, wherein a notch is further provided at the bottom of the through long groove, and radiation protection material is embedded in said notch.

4. The detector device as claimed in claim 1, wherein said first plate is provided with at least one convex stage, a guide slot is formed as an opening in said at least one convex stage,
   a limiting guide wheel is provided in the guide slot and is able to slide along said guide slot.

5. The detector device as claimed in claim 4, further comprising
   a support for adjusting the position of the detector device and locking the detector device,
   wherein said at least one convex stage is further provided with a micrometer head fixed onto the annular rotation disk through the support for adjusting the position of the detector device and locking the detector device.

6. The detector device as claimed in claim 5, wherein said at least one convex stage includes two convex stages, the micrometer head is respectively provided on said two convex stages, said micrometer head is fixed onto the annular rotation table or disk through the support, for adjusting the position of the detector device and locking the detector device.

7. The detector device as claimed in claim 4, wherein the limiting guide wheel is constituted by a high-precision bearing and a pin roll fitted with said high-precision bearing.

8. The detector device as claimed in claim 1, wherein the adjustable positioning base has a projection projecting therefrom in a plane perpendicular to the rotation axis, and the projection has a shape selected from one of an arc, angled line segments, a straight line and multiple sections of arcs.

9. The detector device as claimed in claim 1, wherein the shape of the cross section of the adjustable positioning base on a plane parallel to the rotation axis is substantially an inverted T-shape.

10. The detector device as claimed in claim 1, further comprising:
   a data collection circuit provided at another side on the second plate, which is opposite to the side on which the detector module is provided, for collecting the data produced by the detector module.

11. The detector device as claimed in claim 10, wherein
a radiation protection material for preventing the radiation penetrating therethrough is provided at the side of the second plate on which the detector module is provided.

12. The detector device as claimed in claim 1, wherein the detector module comprises:
a two-level energy detector array constituted by a high energy detector array and a low energy detector array.

13. The detector device as claimed in claim 1, further comprising:
a collimator integrated in front of the detector module, said collimator including:
a base having comb structures opposite to each other in an up-and-down manner; and
a radiation protection partition board provided between said comb structures opposite to each other in an up-and-down manner.

14. The detector device as claimed in claim 1, further comprising:
a shielding cover for covering the adjustable positioning base and detector module, a window being formed as an opening at a place where the shielding faces opposite to the detector module, and a foil being connected to the window to cover said window.

15. The detector device as claimed in claim 1, wherein
a step portion is respectively formed at both ends of the through long groove to be used as a positioning reference of the detector module.

16. A CT inspection system, comprising:
an annular rotation disk rotating about an inspection passage;
a radiation source provided at one side of the annular rotation disk, for generating radiation rays;
a detector device provided at another side of the annular rotation disk substantially opposite to the radiation source, said detector device comprising:
an adjustable positioning base being able to be fixedly connected onto the annular rotation disk; and
a detector module fixedly installed onto the adjustable positioning base,
wherein the adjustable positioning base includes:
a first plate being able to fixedly connected onto the annular rotation disk; and
a second plate extending from the first plate and substantially perpendicular to said first plate, wherein a through long groove is provided at one side of the second plate, perpendicular to a rotation axis of the annular rotation disk; and
wherein the detector module is able to be fixedly installed on the through long groove of the second plate of the adjustable positioning base.

17. The CT inspection system as claimed in claim 16, further comprising
a data collection system for receiving and processing the data signal produced by the detector module.

18. The CT inspection system as claimed in claim 16, further comprising:
a radiation source control unit for supplying electrical power to the radiation source to control the operation of the radiation source.

19. The CT inspection system as claimed in claim 16, wherein
the radiation source is one of an X-ray source, an isotope radiation source and a gamma-ray source.

20. The CT inspection system as claimed in claim 16, wherein
a zigzag structure is provided at the top of one side of the second plate, said zigzag structure is formed by alternating convex and concave portions, and said concave portions are used for receiving transmission wires of the detector module.

21. The CT inspection system as claimed in claim 16, wherein
said first plate is provided with at least one convex stage, a guide slot is formed as an opening in said at least one convex stage, and
a limiting guide wheel is provided in the guide slot and is able to slide along said guide slot.

22. The CT inspection system as claimed in claim 21, wherein
said at least one convex stage is further provided with a micrometer head fixed onto the annular rotation disk through a support for adjusting the position of the detector device and locking the detector device.

23. The CT inspection system as claimed in claim 21, wherein
said at least one convex stage includes two convex stages, the micrometer head is respectively provided on said two convex stages, said micrometer head is fixed onto the annular rotation table or disk through the support, for adjusting the position of the detector device and locking the detector device.

24. The CT inspection system as claimed in claim 16, wherein
a projection, which the adjustable positioning base projects on the horizontal plane, has a shape selected from one of an arc, angled line segments, a straight line and multiple sections of arcs.

25. The CT inspection system as claimed in claim 16, wherein
on a cross section of the adjustable positioning base, which is taken along with a linear direction connecting the target of the radiation source to the detector device, the adjustable positioning base has a substantially inverted T-shape.

26. The CT inspection system as claimed in claim 16, further comprising:
a two-level energy detector array constituted by a high energy detector array and a low energy detector array.

27. The CT inspection system as claimed in claim 16, further comprising:
a collimator integrated in front of the detector module, said collimator including:
a comb shaped base; and
a radiation protection partition board,
wherein the radiation protection partition board is inserted into said base to form a grid-typed structure.

28. The CT inspection system as claimed in claim 16, further comprising:
a shielding cover for covering the adjustable positioning base and detector module, a window is formed as an opening at a place where the shielding faces opposite to the detector module, and a foil is connected to the window to cover said window.

29. The CT inspection system as claimed in claim 28, wherein
a step portion is respectively formed at both ends of the through long groove to be used as a positioning reference of the detector module.

* * * * *